(12) United States Patent
Fowler et al.

(10) Patent No.: US 8,227,508 B2
(45) Date of Patent: Jul. 24, 2012

(54) DIETARY AND PHARMACEUTICAL COMPOSITIONS CONTAINING CARNOSOL AND/OR ROSMANOL AND THEIR USES

(75) Inventors: Ann Fowler, Rheinfelden (CH); Regina Goralczyk, Grenzach-Wyhlen (DE); Claus Kilpert, Mannheim (DE); Hasan Mohajeri, Egg b. Zuerich (CH); Daniel Raederstorff, Flaxlanden (FR); Antoine De Saizieu, Brunstatt (FR); Goede Schueler, Eimeldingen (DE); Ying Wang-Schmidt, Stallikon (CH); Christof Wehrli, Witterswil (CH)

(73) Assignees: DSM IP Assets B.V., Heerlen (NL); Nestec S.A., Vevey (CH)

( * ) Notice: Subject to any disclaimer, the term of this patent is extended or adjusted under 35 U.S.C. 154(b) by 439 days.

(21) Appl. No.: 12/514,881

(22) PCT Filed: Nov. 22, 2007

(86) PCT No.: PCT/EP2007/010133
§ 371 (c)(1),
(2), (4) Date: May 14, 2009

(87) PCT Pub. No.: WO2008/061755
PCT Pub. Date: May 29, 2008

(65) Prior Publication Data
US 2010/0048688 A1 Feb. 25, 2010

(30) Foreign Application Priority Data
Nov. 24, 2006 (EP) ..................................... 06024386

(51) Int. Cl.
A61K 31/352 (2006.01)
C07D 311/78 (2006.01)
(52) U.S. Cl. ........................................ 514/453; 549/278
(58) Field of Classification Search .................. 514/453; 549/278
See application file for complete search history.

(56) References Cited

U.S. PATENT DOCUMENTS
2001/0056121 A1 12/2001 Kosaka et al.

OTHER PUBLICATIONS

International Search Report for PCT/EP2007/010133 mailed Feb. 27, 2008.
Written Opinion for PCT/EP2007/010133 mailed Feb. 27, 2008.
Graham, "GABA(A) receptor channel pharmacology", *Current Pharmaceutical Design*, vol. 11, No. 15, 2005, pp. 1867-1885, XP002412315.
Rouse, "Ginkgo biloba: Mind, Mood and Memory", *Journal of Applied Nutritional Science*, vol. 6, No. 7, 1998, pp. 1-2, XP002412316.
Anonymous, "Rosemary" Internet Citation, [Online], XP002469261, http://www.minddisorders.com/Py-Z/Rosemary.html, retrieved Feb. 15, 2008.
Anonymous, "Neuroloft" Internet Citation, [Online], XP002469262, httpa://www.evitaminstore.com/catalog/Neuroloft-26997.html, retrieved Feb. 15, 2008.

*Primary Examiner* — Raymond Henley, III
(74) *Attorney, Agent, or Firm* — Nixon & Vanderhye P.C.

(57) ABSTRACT

The present invention refers to carnosol and rosmanol for use (as medicament) in the treatment of a disorder connected to reduced neurotransmission, cognitive dysfunction and/or symptoms caused by headache and/or migraine, as well as to dietary and pharmaceutical compositions and their uses.

5 Claims, 5 Drawing Sheets

Figure 1: Compounds of the formulae I (carnosol) and II (rosmanol)

Figure 2A: carnosol

Figure 2B: sarcosine

Figure 2C: ORG24598

Figure 2D: ALX5407

DIETARY AND PHARMACEUTICAL COMPOSITIONS CONTAINING CARNOSOL AND/OR ROSMANOL AND THEIR USES

This application is the U.S. national phase of International Application No. PCT/EP2007/010133 filed 22 Nov. 2007 which designated the U.S. and claims priority to European Patent Application No. 06024386.2 filed 24 Nov. 2006, the entire contents of each of which are hereby incorporated by reference.

BRIEF DESCRIPTION OF THE INVENTION

The present invention refers to carnosol and rosmanol for use as medicaments for the treatment of disorders connected to impaired, i.e. reduced, neurotransmission. In addition, it relates to dietary and pharmaceutical compositions containing carnosol and/or rosmanol and their uses.

BACKGROUND OF THE INVENTION

It is well known that impaired neurotransmission, e.g. low neurotransmitter levels, is connected to mental diseases, such as depression and generalised anxiety disorder (GAD), increased susceptibility to stress and cognitive dysfunction.

Compounds that increase neurotransmitter levels in the brain and thus enhance their transmission, can exhibit antidepressant properties and exert beneficial effects on a variety of other mental disorders (*Neurotransmitters, Drugs and Brain Function* R. A. Webster (ed), John Wiley & Sons, New York, 2001, p. 187-211, 289-452, 477-498). The main neurotransmitters are serotonin, dopamine, noradrenaline (=norepinephrine), acetylcholine, glutamate and gamma-aminobutyric acid (GABA). Those neurotransmitters of particular relevance to mood-related disorders include serotonin, noradrenaline and dopamine, while glutamate and acetylcholine neurotransmission are involved in cognitive function. Enhanced or prolonged neurotransmission is achieved by increasing the concentration of the neurotransmitter in the synaptic cleft, through inhibition of re-uptake into the pre-synaptic nerve ending, or by preventing neurotransmitter catabolism by inhibition of degrading enzymes, such as monoamine oxidases (MAOs)-A and -B. Also of interest are the neuropeptides, such as calcitonin gene-related peptide (CGRP).

Antidepressants and Mood-Related Disorders

Tricyclic antidepressants (TCAs), such as imipramine, amitriptyline and clomipramine, inhibit the re-uptake of serotonin and noradrenaline. They are widely regarded as among the most effective antidepressants available, but they have a number of disadvantages because they additionally interact with muscarinic acetylcholine-, histamine- and serotonin-receptors. Side effects resulting from such activities include dry mouth, blurred vision, constipation and urinary retention, in addition to postural hypotension. Most importantly, TCAs are not safe when taken in overdose, frequently showing acute cardiotoxicity.

Another class of antidepressant drugs is the so-called SSRIs (selective serotonin re-uptake inhibitors), including fluoxetine, paroxetine, sertraline, citalopram and fluvoxamine, that block the serotonin transporter (SERT), a high affinity sodium chloride-dependent neurotransmitter transporter that terminates serotonergic neurotransmission by re-uptake of serotonin. They have been proven as effective in the treatment of depression and anxiety as TCAs, but are usually better tolerated. These medications are typically started at low dosages and are increased until they reach a therapeutic level. A common side effect is nausea. Other possible side effects include decreased appetite, dry mouth, sweating, infection, constipation, tremor, yawning, sleepiness and sexual dysfunction.

In addition, compounds that prevent the catabolism of neurotransmitters more broadly by inhibiting MAOs-A and -B exhibit antidepressant effects. MAOs catalyse the oxidation of amine group-containing neurotransmitters such as serotonin, noradrenaline and dopamine.

Furthermore, modulators of neurotransmission can thus exert pleiotropic effects on mental and cognitive functions.

There is a need for compounds for the treatment or prevention of mental diseases and/or disorders which do not show the negative side effects of known antidepressants. Many patients are interested in alternative therapies which could minimise the side effects associated with high doses of drugs and yield additive clinical benefits. Severe depression is a long-lasting and recurring disease, which is usually poorly diagnosed. Furthermore, many patients suffer from mild or moderately severe depression. Thus, there is an increasing interest in the development of compounds, as well as pharmaceutical and/or dietary compositions, which may be used to treat mental diseases/disorders or to prevent the development of mental diseases/disorders, such as depression and dysthymia, in people at risk, to stabilise mood and achieve emotional balance.

Patients often suffer either as comorbidity to depression, or alone, from GAD, which is a highly prevalent anxiety condition and chronic illness in primary care (~10% of patients) (Wittchen, et al 2005 *Eur. Neuropsychopharm.* 15:357-376). Patients present themselves to their primary care physician with multiple physical symptoms. GAD is characterised by chronic tension, and anxious worrying and tension (>6 months), which are disabling and uncontrollable, and accompanied by a characteristic hypervigilance syndrome (including restlessness, muscle tension and sleep problems). If untreated, GAD runs a chronic, fluctuating course and tends to become increasingly severe with age. GAD patients suffer from subsyndromal depression and contribute to the highest overall direct and indirect health economic burden of all anxiety and depressive disorders. Despite high GAD incidence, few sufferers are diagnosed, prescribed medication, or receive psychiatric referral; simple diagnostic tools to aid patient recognition and monitoring are needed. Regardless of specific diagnosis, physicians require effective GAD-symptom treatments. SSRIs, such as paroxetine, are effective for GAD treatment (Stocchi et al. 2003, *J. Clin. Psych.*, 63(3): 250-258). Also, systematic reviews and placebo-controlled RCTs (Randomised Clinical Trials) indicate that some SSRIs (escitalopram, paroxetine and sertraline), the SNRI (Selective Noradrenaline Reuptake Inhibitor) venlafaxine, some benzodiazepines (alprazolam and diazepam), the TCA, imipramine, and the 5-HT$_{1A}$ partial agonist, buspirone, are all efficacious in acute treatment. In general, the effect of treatment is often moderate and symptoms reappear when the treatment period is discontinued. Therefore, a continuous long-term treatment or prevention with compounds which have fewer side effects than SSRIs and can be taken over long time periods might be favourable over drug treatment.

Mood disorders and occupational stress can lead to sleep disorders, insomnia, low sleep quality and general disturbances in circadian rhythms (so-called biorhythms); such conditions are often chronic and persistent in nature. Also, dysregulation of circadian rhythms induced by long-haul flights (jet-lag) and shift-work can cause similar symptoms and distress. Therefore, treatment with dietary supplementation to maintain a normal circadian rhythm (that a human or animal is used to) and/or to alleviate and prevent symptoms associated with a disturbed circadian rhythm, such as impairment of cognitive function and memory and mental and physical fatigue, thus improving the overall quality of life and benefiting the vital energy of a person in need thereof, would be most desirable.

Headache and Migraine

The major causes of headache are: tension, migraine, eye strain, dehydration, low blood sugar and sinusitis. Headaches can be classified as primary or secondary headaches. The primary headache disorders, which are not associated with any pathological changes, include migraine, tension-related headaches and cluster headaches. Secondary headache disorders, i.e., those caused by a pathological condition, include any head pain of infectious-, neoplastic-, vascular-, drug-induced-, or idiopathic-origin. Primary headaches, such as migraine and cluster headaches, affect up to 20% of the world's population, with a substantial impact on quality of life. Such are characterised by recurrent unilateral headaches, accompanied by nausea, vomiting and photophobia.

During migraine, trigeminal ganglion nerves are activated and release the neuropeptide, CGRP, resulting in vasodilation and mast cell degranulation, with subsequent release of inflammatory agents. Sensitisation of the trigeminal neurones ensues and resulting nociceptive transmission to the CNS contributes to the pain, nausea and photophobia associated with migraine (see Durham and Russo (1999), *J. Neurosci.*, 19 (9), 3423-3429). There is thus a clear association between headache and the release of CGRP; both migraine and cluster headaches have been shown to be associated with elevated plasma CGRP levels, which are restored to normal after pain has been alleviated.

Furthermore, activation of the trigeminovascular nociceptive pathway may be facilitated by low serotonergic activity (Hamel (2007), *Cephalalgia*, 27 (11):1293-1300), while treatment with the triptans (e.g. sumatriptan), which activate the $5-HT_{1B/1D}$ receptor, can relieve an acute migraine attack by reducing CGRP levels (Edvinsson, L. et al 2007, *CNS Neurol. Disord. Drug Targets*, 6(4): 240-246). Additionally, small molecule CGRP antagonists, without cardiovascular side-effects, have been shown to be efficacious in treating migraine (Edvinsson, L., 2007, *Expert Opin. Ther. Targets*, 11 (9): 1179-88). Blockade of the CGRP receptor is also effective in the prevention and treatment of menopausal flushing.

Cognition, Learning and Memory

As mentioned above, maintenance and modulation of mood primarily involve the serotonin-, noradrenaline- and dopamine-neurotransmitter systems, while acetylcholine, acting on nicotinic and muscarinic receptors, plays a role in cognitive processes, including conscious awareness, attention and working memory. Cholinergic agonists are known to improve memory whereas antagonists, generally, impair memory. Importantly, in addition to the involvement of acetylcholine receptor systems in neuropsychiatric disorders, such as attention-deficit hyperactivity disorder, Alzheimer's- and Parkinson's-diseases, there is evidence for nicotinic receptor-mediated cognitive enhancement in non-psychiatric healthy humans, while increased cognitive impairment can occur following co-administration of a muscarinic- and a nicotinic-antagonist. Similarly, inhibition of acetylcholinesterase, the metabolising enzyme for acetylcholine, can be effective in treating cognitive deficits associated with Alzheimer's disease, in addition to improving cognitive performance in healthy subjects.

Furthermore, long-term potentiation (LTP), the term used to describe long-lasting enhancement of synaptic transmission and being widely considered to be one of the major mechanisms by which memories are formed and stored in the brain, primarily involves the N-methyl-D-aspartate (NMDA) receptor complex and the α-amino-3-hydroxy-5-methyl-4-isoxazole propionic acid (AMPA) receptor, both of which bind the major excitatory neurotransmitter, glutamate. In addition to glutamate, the NMDA receptor requires a co-agonist, glycine, in order to modulate receptor function. Glycine transporters (GlyT-1 and -2) play an important role in the termination of postsynaptic glycinergic actions and maintenance of low extracellular glycine concentrations, by reuptake of glycine into presynaptic nerve terminals or glial cells.

There is an increasing interest in the development of compounds, as well as nutraceutical compositions, that may be used to improve learning, memory and alertness, in both elderly and young people, individuals who need especially high memory and attention in their daily work, including students, construction workers, drivers, pilots, physicians, salespeople, executives, housewives, "high performance professionals" and people who are under mental or daily stress as well as persons who are prone to psychiatric instability, such as schizophrenia.

Thus, a compound or nutraceutical composition which enhances NMDA receptor function, enabling improvements in learning, memory and alertness, in addition to enhancing activity of serotonin, noradrenaline and dopamine, enabling improved mood, would be highly desirable.

DETAILED DESCRIPTION OF THE INVENTION

It has been found, in accordance with this invention, that carnosol, rosmanol and mixtures thereof can be used as medicaments for the treatment of a disorder connected to reduced neurotransmission.

In another aspect, the invention relates to the use of an effective amount of carnosol, or rosmanol, or any mixture thereof, for the manufacture of a composition for the treatment of a disorder connected to reduced neurotransmission, particularly for the manufacture of an antidepressant, a mood/vitality improver, a stress reliever, a condition improver, a reducer of anxiety, a reducer of obsessive-compulsive behaviour, a relaxant, a sleep improver and/or an insomnia alleviator and a cognitive enhancer. Furthermore, such a composition can also be used as a headache and/or migraine alleviator.

In still another aspect, the invention relates to a dietary composition containing an effective amount of carnosol and/or rosmanol as well as to a pharmaceutical composition containing at least an effective amount of carnosol and/or rosmanol and a conventional pharmaceutical carrier.

Furthermore, the invention relates to a method for the treatment of a disorder connected to reduced neurotransmission in animals including humans, said method comprising administering an effective dose of carnosol and/or rosmanol to animals including humans which are in need thereof.

Animals in the context of the present invention include humans and encompass mammals, fish and birds. Preferred animals are humans, pet and companion animals and farm animals. Examples of pet and companion animals are dogs, cats, birds, aquarium fish, guinea pigs, (jack) rabbits, hares and ferrets. Examples of farm animals are fish, pigs, horses, ruminants (cattle, sheep and goats) and poultry.

More preferred are (4aR,9S,10aS)-carnosol and (4aR,9S,10aS)-rosmanol.

The term "rosmanol"/"carnosol" also encompasses any material or extract of a plant containing it or them in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract. The terms "material of a plant" and "plant material" used in the context of the present invention mean any part of a plant.

"Carnosol" means the racemic mixture as well as pure (4aR,9S,10aS)-carnosol or pure (4aS,9R,10aR)-carnosol or any mixture or diastereoisomer of them. Carnosol can be isolated from plants including sage, Greek sage and rosemary. Therefore, any material or extract of these plants or any other plant material or extract containing carnosol in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression. "Carnosol" means both "natural" (isolated) and "synthetic" (manufactured) carnosol.

The synthesis of carnosol is described in several articles, i.e. in *Tetrahedron* 2003, 59(18): 3297-3305.

"Rosmanol" means the racemic mixture as well as pure (4aR,9S,10aS)-rosmanol or pure (4aS,9R,10aR)-rosmanol or any mixture or diastereoisomer of them. Rosmanol can be isolated from plants including sage, marjoram, rosemary, thyme, *Salvia* sp., and *Lepechinia* sp. Therefore, any material or extract of these plants or any other plant material or extract containing rosmanol in an amount of at least 30 weight-% (i.e. from 30 to 100 weight-%), preferably in an amount of at least 50 weight-% (i.e. from 50 to 100 weight-%), more preferably in an amount of at least 70 weight-% (i.e. from 70 to 100 weight-%), most preferably in an amount of at least 90 weight-% (i.e. from 90 to 100 weight-%), based on the total weight of the plant material or extract, is also encompassed by this expression. "Rosmanol" means both "natural" (isolated) and "synthetic" (manufactured) rosmanol.

The synthesis of rosmanol is described e.g. in *J. Nat. Prod.* 2002, 65(7):986-989.

Carnosol and/or rosmanol, either as pure compounds or as components of plant materials or plant extracts can be used in dietary and pharmaceutical compositions for the treatment of a disorder connected to reduced neurotransmission.

In the context of this invention "treatment" also encompasses co-treatment as well as prevention. "Prevention" can refer to either the first occurrence (primary prevention) or to a recurrence (secondary prevention).

Thus, the present invention is also directed to a method for the prevention of a disorder connected to reduced neurotransmission in animals including humans, said method comprising administering an effective dose of carnosol or rosmanol or any mixture of them to animals including humans which are in need thereof. In this regard an effective dose of carnosol and/or rosmanol, may especially be used for maintaining the mental well-being, for maintaining a balanced cognitive function, for helping to reduce the risk of mood swings, for helping to retain a positive mood and for supporting cognitive wellness, for helping to maintain a good sleep quality and for helping to minimise symptoms related to headache and/or migraine.

In the context of this invention the term "disorder" also encompasses diseases.

Medicaments/compositions for the treatment of disorders connected to reduced neurotransmission encompass antidepressants, mood/vitality improvers, stress relievers, condition improvers, cognitive enhancers, anxiety reducers and obsessive-compulsive behaviour reducers, relaxants, sleep improvers and/or insomnia alleviators and headache and/or migraine alleviators. They all improve, enhance and support neurotransmission, especially in the central nervous system, and therefore alleviate mental dysfunction.

Antidepressants are medicaments/compositions for treating mental-, behavioural- and emotional/affective-, neurotic-, neurodegenerative-, eating- and stress-related-disorders, such as unipolar depression, bipolar depression, acute depression, chronic depression, subchronic depression, dysthymia, postpartum depression, premenstrual dysphoria/syndrome (PMS), climacteric depressive symptoms, aggression, attention deficit disorders, social anxiety disorders, seasonal affective disorders and anxiety (disorders), such as GAD, fibromyalgia syndrome, post-traumatic stress disorders, panic disorders and obsessive-compulsive disorders, restless leg syndrome, nervousness, migraine/primary headaches and pain in general, emesis, bulimia, anorexia nervosa, binge eating disorder, gastrointestinal disorders, burn-out syndrome and irritability.

Antidepressants can also be used for (the manufacture of compositions for) primary and secondary prevention and/or the treatment of neurocognitive impairment. Furthermore they are also effective in the treatment of depressive symptoms or other symptoms related to disturbed neurotransmission occurring as comorbidity in chronic diseases, such as cardiovascular diseases, strokes, cancer, Alzheimer's disease, Parkinson's disease and others.

Carnosol and/or rosmanol as well as (mixtures of) plant materials and plant extracts containing them (especially in an amount of at least 30 weight-%, preferably in an amount of at least 50 weight-%, more preferably in an amount of from 70 to 90 weight-%, most preferably in an amount of at least 90 weight-%, based on the total weight of the plant material or extract), and dietary/pharmaceutical compositions containing them are thus suitable for the treatment of animals including humans.

In a further embodiment of the present invention carnosol and/or rosmanol find use as mood improvers in general as well as for the manufacture of compositions for such use (plant materials/extracts containing them in an amount of at least 70 weight-%, preferably in an amount of at least 90 weight-%, based on the total weight of the plant material or extract; dietary/pharmaceutical compositions). "Mood improver", "emotional wellness booster" or "vitality improver" means that the mood of a person treated with it is enhanced, that self esteem is increased and/or that negative thoughts and/or negative tension are/is reduced. It also means that the emotions are balanced and/or that general, especially mental, well-being and vitality is improved or maintained, as well as that the risk of mood swings is (helped to be) reduced and that a positive mood is (helped to be) retained.

Carnosol or rosmanol or any mixture of them can also be used in general as anxiety reducers and/or obsessive-compulsive behaviour reducers for animals including humans; preferably for humans, pet animals and farm animals.

"Anxiety reducer" means that chronic tension and anxious worrying and tension are lessened or alleviated. Hypervigilance syndrome, including restlessness, muscle tension and sleep problems, are reduced or relieved. Social—and other phobias are reduced or resolved. In general, the social environment is experienced as less threatening. The person is emotionally relaxed, experiences comfort and enjoys company and contact with other people.

"Relaxant", "sleep improver" or "insomnia alleviator" means improving sleep onset and helping a person to easily enter sleep, to maintain an undisrupted sleep throughout the night. It also means that circadian rhythm-associated sleep disturbances due to jet-lag or shift work are corrected and symptoms associated with sleeplessness, i.e. impairment of cognitive function and memory, mental and physical fatigue, dreaminess, are abolished or relieved and the overall quality of life and vital energy are improved.

Moreover, carnosol or rosmanol as well as compositions comprising an effective dose of it/them are useful for the treatment, prevention and alleviation of stress-related symptoms, for the treatment, prevention and alleviation of symptoms related to work overload, exhaustion and/or burn out, for the increase of resistance or tolerance to stress and/or to favour and facilitate relaxation in normal healthy individuals, i.e. such compositions have an effect as "stress relievers".

A further embodiment of the present invention relates to the use of carnosol and/or rosmanol and to the use of compositions containing it/them (plant materials/extracts containing it/them in an amount of at least 70 weight-%, preferably in an amount of at least 90 weight-%, based on the total weight of the plant material or extract; dietary/pharmaceutical compositions) as "condition improvers", i.e. as means to reduce irritability and tiredness, to reduce, prevent or alleviate physical and mental fatigue, and to increase energy in more general terms, especially to increase the brain energy production, in diseased or normal healthy individuals. Moreover for cognition improvement in general, thus acting as "cognitive enhancers", and especially for maintenance or improvement of attention and concentration, of memory and the capacity for remembering, of learning ability, language processing, problem solving and intellectual functioning; for improvement of short-term memory; for increasing mental alertness; for enhancing mental vigilance; for reducing mental fatigue; for supporting cognitive wellness and for maintaining balanced cognitive function. In addition, such compositions can be used as "headache and/or migraine alleviators", i.e. as a means to reduce symptoms associated with headache and/or migraine, such as head pain, nausea, disturbed vision and photophobia, as well as for the regulation of hunger and satiety and for the regulation of motor activity.

Veterinary Uses

Pets and farm animals can be in conditions in need of enhanced or improved neurotransmission, which can be provided by the present invention. Animals may exhibit adverse behavioural and/or physiological reactions to stressful situations; animals raised in mass production environments, or being transported under unfavourable conditions, can display a decline in meat or milk quantity or quality; stressed poultry can resort to feather-picking, reduced egg laying and cannibalism. Many animals can become aggressive or display stereotypic-, anxiety- and obsessive-compulsive-behaviours under adverse housing or transport conditions.

Thus, another aspect of this invention is veterinary uses of carnosol and/or rosmanol and compositions containing it/them as dietary/pharmaceutical compositions.

In a preferred embodiment of the present invention, carnosol and/or rosmanol, or plant materials or extracts containing either or both of them, are administered for preventing stress in farm animals and mass production livestock husbandry, during transport to slaughter and/or for preventing loss of quality of meat of said farm animals under such circumstances. The farm animals are preferably poultry, cattle, sheep, goats and swine.

In another preferred embodiment of the present invention, carnosol and/or rosmanol, or plant materials or extracts containing either or both of them, are administered to poultry for preventing feather-picking and cannibalism resulting in, for example, loss of meat quality and egg production.

Another aspect of this invention is a method for preventing and/or alleviating stress in aquaculture, comprising administering carnosol and/or rosmanol, or plant materials or extracts containing either or both of them, to animals which are in need thereof, wherein the animals are fish or shrimps.

In another preferred embodiment of the present invention, carnosol and/or rosmanol, or plant materials or extracts containing either or both of them, are administered to pets or companion animals for reduction of stress, tension and aggressiveness and compulsive behaviour exhibited under stressful conditions, such as separation, change or loss of owner, during holiday separation and husbandry in so-called "animal hotels" and husbandry in animal shelters or refuges.

Still another aspect of this invention is a method for preventing/reducing symptoms associated with stressful conditions in animals used in the fur industry, preferably minks, foxes and hares.

Preferred Doses and Compositions of the Present Invention

For humans a suitable daily dosage of carnosol or rosmanol or any mixture of them for the purposes of the present invention may be within the range of from 0.001 mg per kg body weight to about 20 mg per kg body weight per day. More preferred is a daily dosage of from about 0.01 to about 10 mg per kg body weight, and especially preferred is a daily dosage of from about 0.05 to 5.0 mg per kg body weight. The amount of a plant material or plant extract containing either carnosol or rosmanol or both of them can be calculated accordingly.

The term "dietary compositions" comprises any type of (fortified) food/feed and beverages including also clinical nutrition and dietary supplements. The dietary compositions according to the present invention may further contain protective hydrocolloids, binders, film-forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste-masking agents, weighting agents, jellyfying agents, gel-forming agents, antioxidants and antimicrobials.

Beside a pharmaceutically acceptable carrier and at least either carnosol or rosmanol, the pharmaceutical compositions according to the present invention may further contain conventional pharmaceutical additives and adjuvants, excipients or diluents, flavouring agents, preservatives, stabilisers, emulsifying agents, buffers, lubricants, colorants, wetting agents, fillers, and the like. The carrier material can be an organic or inorganic inert carrier material suitable for oral/parenteral/injectable administration.

The dietary and pharmaceutical compositions according to the present invention may be in any galenic form that is suitable for administering to the animal body including the human body, especially in any form that is conventional for oral administration, e.g. in solid form such as (additives/supplements for) food or feed, food or feed premix, fortified food or feed, tablets, pills, granules, dragées, capsules and effervescent formulations, such as powders and tablets, or in liquid forms, such as solutions, emulsions or suspensions as e.g. beverages, pastes and oily suspensions. The pastes may be filled into hard- or soft-shell capsules. Examples for other application forms are those for transdermal, parenteral or injectable administration. The dietary and pharmaceutical compositions may be in the form of controlled (delayed) release formulations.

Examples for fortified foods are cereal bars and bakery items such as cakes and cookies.

Beverages encompass non-alcoholic and alcoholic drinks as well as liquid preparations to be added to drinking water and liquid food. Non-alcoholic drinks are e.g. soft drinks, sport drinks, fruit juices, lemonades, near-water drinks (i.e. water-based drinks with a low calorie content), teas and milk-based drinks. Liquid foods are e.g. soups and dairy products (e.g. muesli drinks).

In solid dosage unit preparations for humans, carnosol or rosmanol or any mixture of them, is suitably present in an amount in the range of from about 0.1 mg to about 1000 mg, preferably in the range of from about 1 mg to about 500 mg per dosage unit.

In dietary compositions, especially in food and beverages for humans, carnosol or rosmanol or any mixture of them, is suitably present in an amount in the range of from about 0.0001 (1 mg/kg) to about 5 weight-% (50 g/kg), preferably from about 0.001% (10 mg/kg) to about 1 weight-%, (10 g/kg) more preferably from about 0.01 (100 mg/kg) to about 0.5 weight-% (5 g/kg), based upon the total weight of the food or beverage.

In food and drinks, the range is from 10 to 30 mg per serving, i.e. 120 mg per kg food or drink.

For animals excluding humans a suitable daily dosage of carnosol or rosmanol, or any mixture of them, may be within the range of from 0.001 mg per kg body weight to about 1000 mg per kg body weight per day. More preferred is a daily dosage in the range of from about 0.1 mg to about 500 mg per kg body weight, and especially preferred is a daily dosage in the range of from about 1 mg to 100 mg per kg body weight.

The invention is illustrated further by the following examples.

EXAMPLES

The carnosol and rosmanol used in the following experiments were synthesised by chemists of DSM Nutritional Products Ltd., Kaiseraugst, Switzerland. All compounds were >95% pure.

The actions of the monoamine neurotransmitters, serotonin, dopamine and noradrenaline, are regulated through their rapid uptake and clearance from synaptic junctions by plasma membrane transport proteins. The monoamine transporters in central monoaminergic neurones are responsible for the recovery of up to 90% of released neurotransmitter and are high affinity targets for a number of psychoactive agents such as cocaine, amphetamine and antidepressants. These agents, by blocking transporters and consequently preventing neuronal uptake, elevate levels of extracellular neurotransmitter concentrations in both the central and peripheral nervous systems, contributing to their behavioural and autonomic effects. Thus, inhibition of uptake of serotonin, dopamine and noradrenaline by carnosol and/or rosmanol is illustrated by the following three examples.

Example 1

Serotonin Uptake Inhibition by Carnosol and Rosmanol

Human embryonic kidney (HEK-293) cells stably expressing the human serotonin re-uptake transporter (hSERT) were obtained from R. Blakely, Vanderbilt University, USA. The cells were routinely grown in Dulbecco's Modified Eagle's Medium (Bioconcept) containing 10% dialysed foetal calf serum (Invitrogen), penicillin, streptomycin, L-glutamine and the antibiotic G418 and passaged by-trypsinisation. On the day of assay, cells from 80% confluent flasks were harvested by gentle washing with warm phosphate buffered saline (PBS). Cells were then washed once by centrifugation and re-suspended in Krebs-Ringer bicarbonate buffer (Sigma) supplemented with 35 µM pargyline, 2.2 mM $CaCl_2$, 1 mM ascorbic acid and 5 mM N-2-hydroxyethylpiperazine-N'-2-ethanesulfonic acid (HEPES buffer), at a concentration of 10,000 cells in 160 µl of buffer, and aliquoted into round-bottomed polypropylene 96-well microtitre plates (Corning) at 10,000 cells per well. Serotonin uptake into the cells was determined by addition of radio-labelled [$^3$H]-serotonin (GE Healthcare) at a concentration of 20 nM, and incubation for 40 minutes at 37° C. with gentle shaking. At the end of this time unincorporated label was removed by filtration though Unifilter 96 GF/B plates (Perkin Elmer) using a Tomtec Mach III M cell harvester. The incorporated serotonin retained on the plates was quantified by liquid scintillation counting using Microscint-40/Topcount (Perkin Elmer).

The effect of carnosol, rosmanol and the reference compound, fluoxetine, on serotonin uptake was determined by their inclusion in the assay at a range of concentrations (carnosol and rosmanol: 0.003-100 µM; fluoxetine: 0.03 nM-1 µM) for 10 minutes prior to and during the addition of [$^3$H] serotonin. Serotonin uptake via the transporter was inhibited by each of them in a dose-dependent manner. The calculated $IC_{50}$ values for inhibition of serotonin uptake by each of them are shown in Table 1.

TABLE 1

Inhibition of serotonin uptake into transfected HEK-293 cells by carnosol, rosmanol and the reference compound, fluoxetine. Data is shown as mean ± s.e.m. (n = 2).

| Compound | $IC_{50}$ |
| --- | --- |
| Carnosol | 26.6 ± 6.9 µM |
| Rosmanol | 23.2 ± 9.7 µM |
| Fluoxetine | 5 nM |

Example 2

Dopamine Uptake Inhibition by Carnosol

Chinese hamster ovary (CHO)-K1 cells expressing the human dopamine transporter (hDAT) were plated before the assay. Cells ($2\times10^5$/ml) were incubated with carnosol and/or vehicle in modified Tris-HEPES buffer (5 mM Tris-HCl, 7.5 mM HEPES, pH 7.1), further containing 120 mM NaCl, 5.4 mM KCl, 1.2 mM $CaCl_2$, 1.2 mM $MgSO_4$, 5 mM D-glucose and 1 mM ascorbic acid, at 25° C. for 20 minutes before addition of 50 nM [$^3$H]-dopamine for 10 minutes. Specific signal was determined in the presence of 10 µM nomifensine (dopamine reuptake inhibitor). Cells were then solubilised with 1% SDS lysis buffer. Reduction of [$^3$H]-dopamine uptake by 50 percent or more ($\geqq$50%) relative to vehicle controls indicated significant inhibitory activity. Carnosol was tested at ten concentrations (0.00316-100 µM) and nomifensine at five concentrations (0.001-0.1 µM). These same concentrations were concurrently applied to a separate group of cells and evaluated for possible compound-induced cytotoxicity only if significant inhibition of uptake was observed.

TABLE 2

Measured $IC_{50}$ values for inhibition of dopamine reuptake into transfected CHO-Ki cells by carnosol and the reference compound, nomifensine.

| Compound | $IC_{50}$ |
| --- | --- |
| Carnosol | 10.3 µM |
| Nomifensine | 0.0104 µM |

Example 3

Noradrenaline Uptake Inhibition by Carnosol

Madin Darby canine kidney (MDCK) cells, stably expressing the human noradrenaline transporter (hNAT), were plated one day before the assay. The cells (2×10$^5$/ml) were preincubated with carnosol and/or vehicle in modified Tris-HEPES buffer (5 mM Tris-HCl, 7.5 mM HEPES, pH 7.1) further containing 120 mM NaCl, 5.4 mM KCl, 1.2 mM CaCl$_2$, 1.2 mM MgSO$_4$, 5 mM D-glucose and 1 mM ascorbic acid, at 25° C. for 20 minutes, then 25 nM [$^3$H]-noradrenaline was added for 10 minutes incubation. Cells in each well were then rinsed twice, solubilised with 1% SDS lysis buffer and the lysate was analysed to determine [$^3$H]-noradrenaline uptake. Specific signal was determined in the presence of 10 µM desipramine (tricyclic antidepressant which inhibits noradrenaline reuptake). Reduction of [$^3$H]-noradrenaline uptake by 50 percent or more ($\geqq$50%) relative to vehicle controls indicated significant inhibitory activity. Carnosol was tested at ten concentrations (0.00316-100 µM) and desipramine at five concentrations (0.5-50 nM). These same concentrations were concurrently applied to a separate group of cells and evaluated for possible compound-induced cytotoxicity only if significant inhibition of uptake was observed.

TABLE 3

Measured $IC_{50}$ values for inhibition of noradrenaline reuptake into transfected MDCK cells by carnosol and the reference compound, desipramine.

| Compound | $IC_{50}$ |
| --- | --- |
| Carnosol | 30.6 µM |
| Desipramine | 1.93 nM |

Example 4

Monoamine Oxidase Inhibition by Carnosol and Rosmanol

The organic amines p-tyramine or benzylamine were used as substrates for the monoamine oxidase A (MAO-A) and B (MAO-B) enzymes respectively. The H$_2$O$_2$ produced by this reaction was quantified by reaction with vanillic acid, catalysed by horse radish peroxidase (HRP).

The reactions were carried out at 37° C. in polystyrene microtitre plates. The MAO enzymes (final concentration 2 U/ml) were mixed with either p-tyramine (Sigma, final concentration 0.5 mM) or benzylamine (Sigma, final concentration 0.5 mM) as appropriate and the chromogenic solution (containing vanillic acid (Fluka), 4-aminoantipyrine (Fluka) and horse radish peroxidase (Sigma), final concentrations 0.25 mM, 0.125 mM and 1 U/ml, respectively) in 0.2 M potassium phosphate buffer, pH 7.6. After 40 min incubation, plates were analysed in a microtitre plate absorbance reader, e.g. Spectramax M5 (Molecular Devices Corporation), at 495 nm.

The effects of carnosol and rosmanol on the monoamine oxidase enzymes were determined by their inclusion in the assay at a range of concentrations between 0.03 and 100 µM for 10 minutes prior to and during the incubation with substrate. To determine the effect of the compounds on the HRP-catalysed portion of the reaction, the MAO enzyme was replaced by H$_2$O$_2$ (Molecular Probes, final concentration 50 µM). The reactions containing MAO-A and MAO-B were both inhibited by carnosol and rosmanol in a dose-dependent manner, whilst the control reaction was unaffected. The measured $IC_{50}$ values for inhibition of monoamine oxidase activity by carnosol and rosmanol are shown in Table 4.

TABLE 4

Inhibition of MAO-A and MAO-B by carnosol and rosmanol. Data is shown as mean ± s.e.m.

| Compound | MAO-A ($IC_{50}$) | MAO-B ($IC_{50}$) |
| --- | --- | --- |
| Carnosol | 4.0 ± 0.1 µM (n = 3) | 106.5 ± 19.9 µM (n = 2) |
| Rosmanol | 3.02 ± 0.48 µM (n = 3) | 73.3 ± 11.3 µM (n = 2) |

Example 5

Glycine Transporter 1 Inhibition by Carnosol and Rosmanol

CHO cells stably expressing the human glycine transporter 1b cDNA (GlyT1) were routinely grown in Dulbecco's Modified Eagle's Medium (Invitrogen, Carlsbad, USA) containing 10% dialysed foetal calf serum, penicillin, streptomycin, proline and the antibiotic G418. Cells were harvested by trypsinisation one day prior to the assay and were seeded in the above mentioned medium. Immediately prior to the assay, the medium was replaced by uptake buffer containing 150 mM NaCl, 1 mM CaCl$_2$, 2.5 mM KCl, 2.5 mM MgCl$_2$, 10 mM Glucose and 10 mM N-2-hydroxyethylpiperazine-N'-2-ethanesulfonic acid (HEPES buffer).

Glycine uptake into the cells was determined by addition of 60 nM radiolabelled [$^3$H]-glycine (Amersham Biosciences GE Healthcare, Slough, UK) and incubation for 30 minutes at room temperature. Following removal of unincorporated label by gentle washing three times with the above buffer, incorporated glycine was quantified by liquid scintillation counting.

Figure 1:
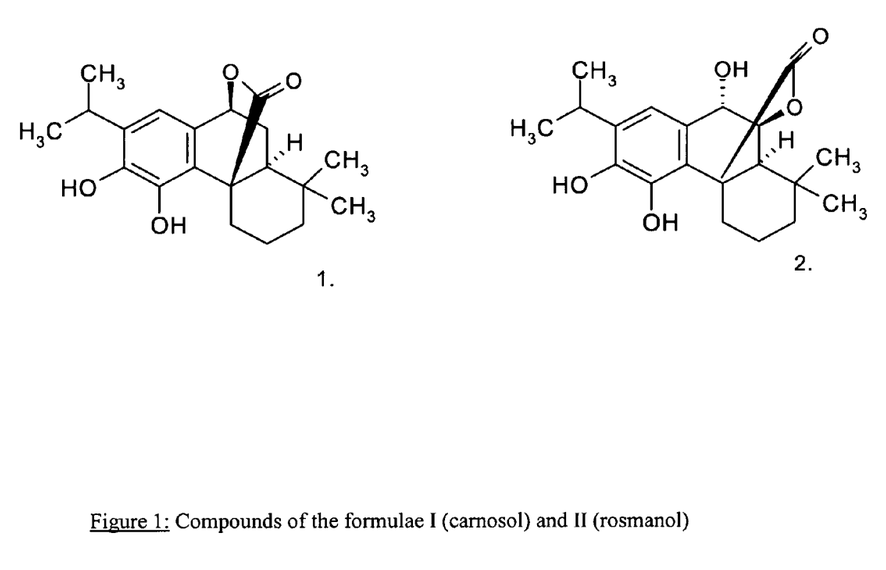
FIG. 1 shows the structures of carnosol (compound of formula I) and rosmanol (compound of formula II).
Figure 2A:
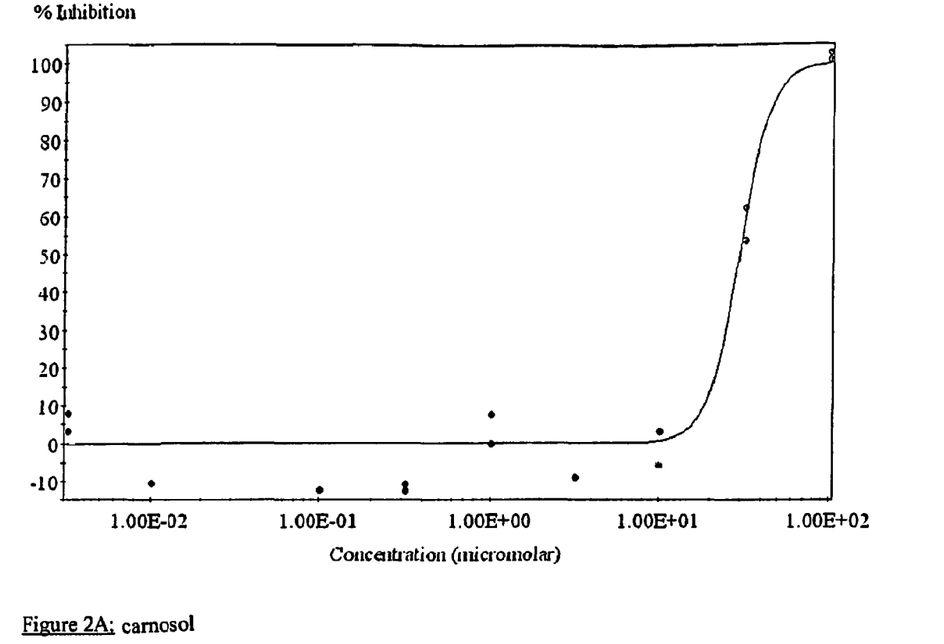
FIG. 2A is a graph showing GlyT1 glycine transporter inhibition for carnosol, as described in Example 5.
Figure 2B:
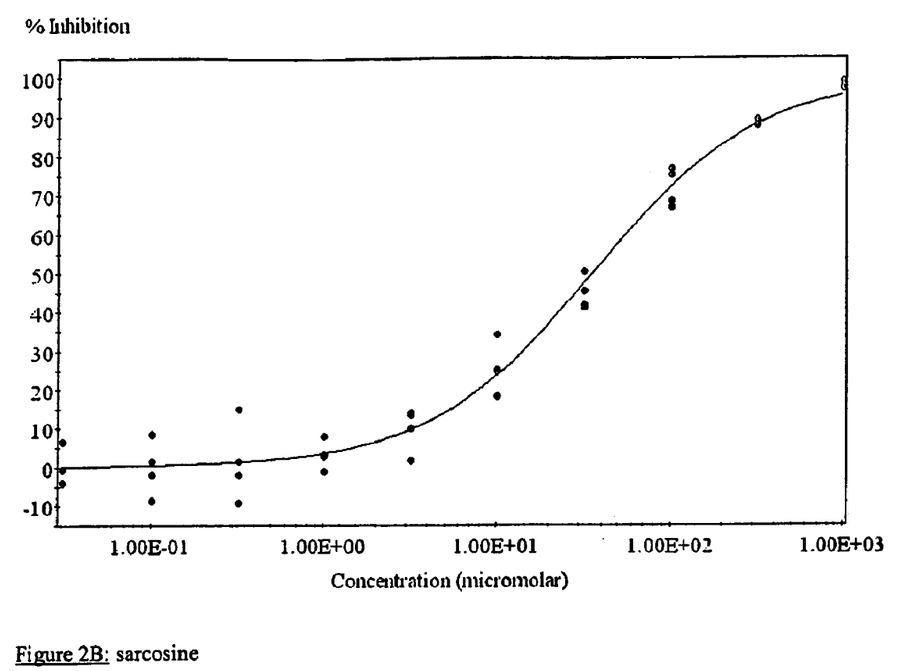
FIG. 2B is a graph showing GlyT1 glycine transporter inhibition for sarcosine, as described in Example 5.
Figure 2C:
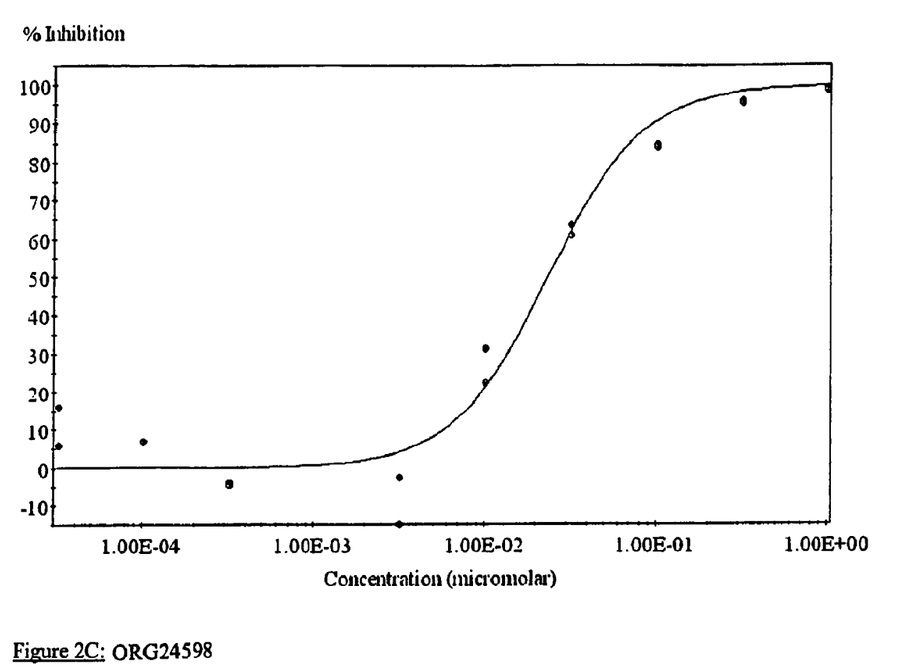
FIG. 2C is a graph showing GlyT1 glycine transporter inhibition for ORG24598 as described in Example 5.
Figure 2D:
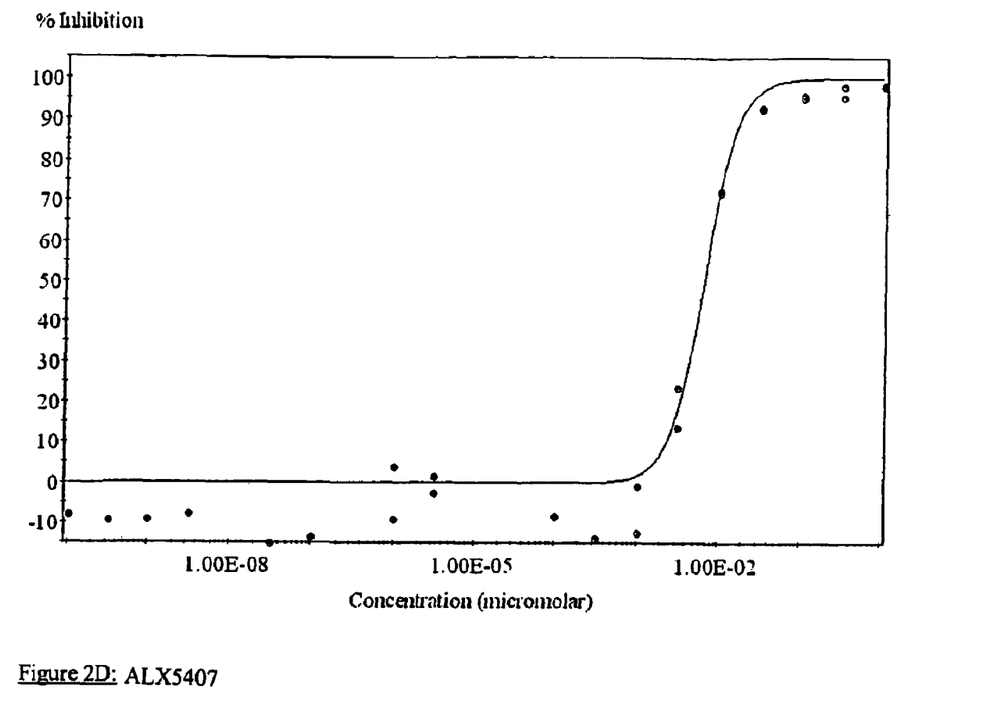
FIG. 2D is a graph showing GlyT1 glycine transporter inhibition ALX5407, as described in Example 5.

Glycine uptake via the GlyT1 transporter was inhibited by the addition of carnosol (0.00316-100 µM) in a dose-dependent manner. Rosmanol, however, was inactive in this assay. Sarcosine, ORG24598 and ALX5407 (all from Sigma, St. Louis, USA) were used as known inhibitors of GlyT1. The measured $IC_{50}$ values for inhibition of glycine uptake and representative dose-response curves are shown in Table 5 and FIG. 2, respectively.

TABLE 5

Measured $IC_{50}$ values for inhibition of glycine uptake into CHO cells by carnosol, rosmanol, sarcosine, ORG24598 and ALX5407.

| Substance | $IC_{50}$ for tritiated glycine uptake |
|---|---|
| carnosol | 29.33 µM |
| rosmanol | inactive |
| sarcosine | 35.9 µM |
| ORG24598 | 0.02 µM |
| ALX5407 | 6.46 nM |

Example 6

Effects of Carnosol and Rosmanol on LTP in Hippocampal Slice Cultures

Seven-day-old Wistar rats were decapitated using a guillotine. In less than 1 minute the skull was opened, the cerebral hemispheres were separated and transferred and both hippocampi were dissected and transferred into ice-cold buffer containing 137 mM NaCl, 5 mM KCl, 0.85 mM $Na_2HPO_4$, 1.5 mM $CaCl_2$, 0.66 mM $KH_2PO_4$, 0.28 mM $MgSO_4$, 1 mM $MgCl_2$, 2.7 mM $NaHCO_3$, 1 mM Kynurenic acid and 0.6% D-glucose.

Transverse hippocampal slices (400 µm) were prepared using a vibrating blade microtome (VT1200S; Leica Microsystems (Schweiz) AG, Heerbrugg, Switzerland) in the same buffer. Hippocampal slices were individually placed on membrane inserts (Millicell Culture Plate Inserts, 0.4 µm) and cultivated at 35° C., 5% $CO_2$, 95% humidity in a medium containing a 1:1 mixture of BME and MEM (both from Invitrogen) containing 25% heat-inactivated horse serum, 1× GlutaMAX, 1× Penicillin/Streptomycin, 0.6% glucose and 1 mM Kynurenic acid (Stoppini, Buchs and Muller (1991), *J. Neurosci. Methods*, 37(2), 173-82).

After 48 h in culture, synaptic NMDA receptors were activated by addition of carnosol or rosmanol for 15 min in 140 mM NaCl, 5 mM KCl, 1.3 mM $CaCl_2$, 25 mM HEPES (pH 7.3), 33 mM D-glucose and 0.02 mM bicuculline methiodide. Sarcosine (100 µm) and ALX5407 (20 nM) were used routinely as positive controls. An additional positive control comprised the addition of 200 µM glycine to sister cultures. After the treatments, sections were washed and fixed for immunohistochemistry. Markers of enhanced synaptic activity, normally associated with long-term potentiation, representing an ex vivo model of learning and memory were quantitated (see Table 6, below).

TABLE 6

Relative activation of synaptic markers after treatment with carnosol or rosmanol in comparison with sister cultures treated with buffer. The activation of any of these markers (or a combination thereof) is observed in classical LTP experiments.

| Substance | pCREB | pMAPK | GluR1 |
|---|---|---|---|
| Carnosol | ± | ++ | 608% |
| Rosmanol | ± | + | 320% |

++++ shows a qualitative maximal activation, ++ and + signify a half-maximal and moderate activation, respectively, while ± demonstrated no change in immunoreactivity; for GluR1; values are shown as percentage of control values.

Treatment of hippocampal cultures with carnosol and rosmanol induced one or more biochemical markers typical for LTP (pCREB: activated form of the cAMP response element binding protein; pMAPK: activated form of the mitogen-activated protein kinase; GluR1: cell surface presence of AMPA receptor 1).

Example 7

CGRP Receptor Inhibition by Carnosol

CGRP is a potent vasodilator in brain vessels and has been implicated in the pathogenesis of migraine headache. The CGRP receptor is especially abundant in the trigeminal vasculature, a network of intracranial vessels associated with sensory neurones of the trigeminal ganglion. Activation of trigeminal sensory neurones and CGRP release are strongly implicated in the pathophysiology of migraine headache. Blockade of the CGRP receptor is effective in the prevention and treatment of migraine, headaches and menopausal flushing.

The effect of carnosol on the agonist site of the human calcitonin gene-related peptide (hCGRP) receptor in transfected CHO cells was investigated using a radioligand binding assay adapted from that described by Aiyar et al. (1996, *J. Biol. Chem.*, 271: 11325-11329).

Briefly, cell membrane homogenates (10 µg protein) were incubated for 90 min at 22° C. with 0.03 nM [$^{125}$I]h-CGRPα in the absence or presence of carnosol (10 µM) in a buffer containing 50 mM HEPES-NaOH (pH 7.4), 10 mM $MgCl_2$, 4 mM KCl, 10 mM NaCl, 1 mM EDTA, 1 µM phosphoramidon, 0.3% BSA and 0.04% bacitracine. Non-specific binding was determined in the presence of 1 µM h-CGRPα. Following incubation, the samples were filtered rapidly under vacuum through glass fibre filters (GF/B, Packard) pre-soaked with 0.3% polyethyleneimine (PEI) and rinsed several times with ice-cold 50 mM Tris-HCl using a 96-sample cell harvester (Unifilter, Packard). The filters were dried then counted for radioactivity in a scintillation counter (Topcount, Packard) using a scintillation cocktail (Microscint 0, Packard). The results are expressed as percentage inhibition of the control radioligand specific binding. The standard reference compound used was h-CGRPα, the natural agonist of the hCGRP receptor.

Binding to the hCGRP receptor was markedly inhibited (54%) by 10 µM carnosol. Thus carnosol can be used in the prevention and treatment of migraine, headache and menopausal flushing.

Example 8

Acetylcholinesterase Inhibition by Carnosol

The main role of acetylcholinesterase is the termination of neurotransmission at the cholinergic synapses by rapid hydrolysis of acetylcholine. Inhibition of this key enzyme is considered to be a useful strategy for the treatment of cognitive dysfunction and memory disorders.

The effect of carnosol on human recombinant acetylcholinesterase activity was quantified by measuring the formation of 5-thio-2-nitrobenzoic acid from acetyl-6-methylthiocholine (AMTCh), as adapted from Ellman et al. (1961, *Biochem. Pharmacol.*, 7: 88-90). Briefly, carnosol (10 µM), reference compound or water (control) were added to a buffer containing 200 mM $NaH_2PO_4/Na_2HPO_4$ (pH 8.0), 5 mg/ml $(NH_4)_2SO_4$, 0.4 mM DTNB and 5 mU enzyme. The enzymatic reaction was then initiated by the addition of the substrate AMTCh at 50 μM. The absorbance was measured immediately (t=0) at λ=405 nm using a microplate reader (MRX, Dynatech or Ultra, Tecan). This measurement was used to detect any compound interference with the spectrophotometric detection at this wavelength. After 30 min incubation at 37° C. (t=30), a second measurement of the absorbance was made at λ=405 nm. The enzyme activity was determined by subtracting the signal measured at t=0 from that measured at t=30. The results are expressed as percentage inhibition of the control enzyme activity. The standard inhibitory reference compound used was neostigmine, tested in each experiment at several concentrations to obtain an inhibition curve from which its $IC_{50}$ value was calculated.

Acetylcholinesterase activity was markedly inhibited (53%) by 10 μM camosol. Thus, carnosol was demonstrated to be an effective acetylcholinesterase inhibitor and can be used for the prevention or treatment of mild cognitive impairment and memory loss.

Example 9

Porsolt's Swim Test

The Forced Swim Test (FST) was first reported in 1977 for screening of antidepressant-like compounds in rats (Porsolt et al 1977 *Nature*, 266:730-732) and, later, modified for testing mice (Porsolt et al 1977 *Arch. Int. Pharmacodynamie*, 229: 327-336). "Behavioural despair" was demonstrated whereby, when forced to swim in a cylinder of water from which there is no escape, rats or mice will initially exhibit vigorous, escape-oriented, activity but eventually only make those minimal movements necessary to keep their heads above water. The test was shown to be sensitive to a range of drugs with known therapeutic activity against depression, some of which had not previously shown efficacy in the existing behavioural models.

In two separate experiments, mice were tested following either i.p. or p.o. administration of carnosol. Mice were individually placed in a cylinder containing water (22° C.) from which they could not escape. The mice were placed in the water for 6 min and the duration of immobility during the last 4 min was measured. Ten to fifteen mice were studied per group. Carnosol was evaluated at 3, 10, 30 mg/kg body weight (i.p. 30 min before the test) or 200, 400, 600 mg/kg body weight (p.o., 24, 5 and 1 h before the test), and compared with vehicle control groups. Imipramine (32 mg/kg i.p., or p.o., respectively), administered under the same experimental conditions, was used as reference substance. Immobility and swimming time were assessed.

TABLE 7

Effects of carnosol and imipramine in the FST in the mouse, following i.p. (−30 min) or p.o. (−24, −5, −1 h) administration.

| Treatment | | | Duration of immobility (% change from control) | |
|---|---|---|---|---|
| carnosol | 3 mg/kg | i.p., −30 min | −26% | ** |
| carnosol | 10 mg/kg | i.p., −30 min | −21% | * |
| carnosol | 30 mg/kg | i.p., −30 min | −18% | * |
| imipramine | 32 mg/kg | i.p., −30 min | −80% | *** |
| carnosol | 200 mg/kg | p.o., −24, −5, −1 h | −9% | NS |
| carnosol | 400 mg/kg | p.o., −24, −5, −1 h | −53% | ** |
| carnosol | 600 mg/kg | p.o., −24, −5, −1 h | −3% | NS |
| imipramine | 32 mg/kg | p.o., −24, −5, −1 h | −48% | ** |

TABLE 7-continued

Effects of carnosol and imipramine in the FST in the mouse, following i.p. (−30 min) or p.o. (−24, −5, −1 h) administration.

| Treatment | Duration of immobility (% change from control) |
|---|---|

Duration of immobility is shown as % change from control, where NS = non-significant, * $p < 0.05$,  $p < 0.01$, * $p < 0.001$ (Student's t-test).

Thus, following i.p. administration, all doses of carnosol tested in the FST significantly reduced immobility behaviour whereas, following p.o. administration, only the intermediate dose (400 mg/kg) significantly reduced immobility. This data thus indicates antidepressant-like activity of carnosol.

Example 10

Marble Burying Test

"Defensive burying" behaviour was demonstrated by rats burying noxious objects, such as drinking spouts filled with an unpleasant-tasting liquid (Wilkie et al, 1979 *J. Exp. Anal. Behav.* 31:299-306.) or shock prods (Pinel et al. *J. Comp. Phys. Psych.* 92:708-712). The marble burying test was devised as a modification of such a test (Poling et al 1981. *J. Expl. Anal. Behav.* 35:31-44). Rats were exposed to individual cages each containing 25 marbles, daily for 10 or 21 consecutive days. The number of marbles buried, on each day of the 10 d period, or 24 h after the 21 d exposure, were counted. The authors reported that the burying of marbles was not determined by novelty, or due to any noxious stimuli.

Marble burying behaviour by mice is reported to be sensitive to a range of minor (e.g. diazepam) and major (e.g. haloperidol) tranquilisers (Broekkamp et al., 1986 *Eur. J. Pharm.*, 126:223-229), in addition to SSRIs (e.g. fluvoxamine, fluoxetine, citalopram), tricyclic antidepressants (e.g. imipramine, desipramine) and selective noradrenaline uptake inhibitors (e.g. reboxetine), at doses which do not induce sedation. The model may reflect either anxiety-like- or obsessive-compulsive-behaviour (see De Boer et al., 2003 *Eur. J. Pharm.* 463:145-161).

The method applied here follows that described by Broekkamp et al. (1986). Mice (n=15 per treatment group) were individually placed in transparent plastic cages (33×21× 18 cm) with 5 cm of sawdust on the floor and 25 marbles (diameter 1 cm) grouped in the centre of the cage. A second, up-turned, cage served as a lid. The number of marbles covered by sawdust (by at least two-thirds) was counted at the end of the 30-min test period. Tests were performed by investigators blind to the drug treatment protocol.

Prior to testing, all test cages and marbles were "impregnated" by leaving 10 naive mice in each cage for 15 minutes.

Carnosol (3, 10 and 30 mg/kg) and rosmanol (10, 30 and 100 mg/kg) were administered i.p. 30 min before the test, and compared with a vehicle control group. Fluoxetine (32 mg/kg), administered under the same experimental conditions, was used as a reference substance.

TABLE 8

Effects of carnosol, rosmanol and fluoxetine in the marble burying test in the mouse.

| Treatment (i.p., −30 min) | | Number of marbles buried (% change from control) | |
|---|---|---|---|
| carnosol | 3 mg/kg | −12% | NS |
| carnosol | 10 mg/kg | −10% | NS |
| carnosol | 30 mg/kg | −41% | ** |
| rosmanol | 10 mg/kg | −21% | NS |
| rosmanol | 30 mg/kg | −12% | NS |
| rosmanol | 100 mg/kg | −55% | *** |
| fluoxetine | 32 mg/kg | −92% | *** |

Burying behaviour (i.e. number of marbles at least two-thirds covered by sawdust) is shown as % change from control, where NS = non-significant,  $p < 0.01$, * $p < 0.001$ (Student's t-test).

The highest doses of carnosol (30 mg/kg) and rosmanol (100 mg/kg) tested clearly and significantly reduced marble burying behaviour in a similar manner to the SSRI fluoxetine, thus indicating anxiolytic-like activity of both compounds.

Example 11

Effect of Carnosol in the Four Plates Test

The method, which detects anxiolytic activity, follows that described by Aron et al (1971, *Neuropharmacology*, 10:459-469). Anxiolytics (benzodiazepines) increase the number of punished crossings. Animals were placed individually in a white plastic enclosure containing a floor consisting of 4 metal plates connected to an electric shock generator (Apelex: type 011346). Each mouse was left to explore freely for 15 seconds. Then, every time it crossed from one plate to another, it received a weak electric shock (2.5 mA, 1.5 s). The number of punished crossings was counted during a 1 minute test. 15 mice were studied per group. The test was performed blind.

Carnosol was evaluated at 3 doses (200, 400, 600 mg/kg), administered p.o. 24 h, 5 h and 1 h before the test, and compared with a vehicle control (corn oil) group.

Clobazam (32 mg/kg p.o.), administered 1 h before the test, was used as reference substance. Mice in this group received additional administrations of vehicle at 24 h and 5 h before the test in order to maintain experimental blinding.

TABLE 9

Effects of carnosol in the Four Plates Test in the mouse.

| TREATMENT (mg/kg) p.o. −24 h and −5 h | TREATMENT (mg/kg) p.o. −1 h | NUMBER OF PUNISHED CROSSINGS mean ± s.e.m. | | | p value | % change from control |
|---|---|---|---|---|---|---|
| Vehicle | Vehicle | 2.8 | ± | 0.2 | — | — |
| Carnosol (200) | Carnosol (200) | 3.5 | ± | 0.3 | NS | 0.0713 | +25% |
| Carnosol (400) | Carnosol (400) | 3.7 | ± | 0.3 | * | 0.0196 | +32% |
| Carnosol (600) | Carnosol (600) | 3.1 | ± | 0.4 | NS | 0.4406 | +11% |
| Vehicle | Clobazam (32) | 6.1 | ± | 0.5 | *** | <0.0001 | +118% |

Number of punished crossings is shown as mean ± s.e.m. and as % change from control, where NS = non-significant,
* $p < 0.05$ and
*** $p < 0.001$ (Student's t-test).

Carnosol (200, 400 and 600 mg/kg) globally increased the number of punished crossings, as compared with vehicle control (+25%, +32% and +11%, respectively), significantly so at 400 mg/kg ($p < 0.05$). These results suggest that carnosol has weak but significant anxiolytic-like activity at 400 mg/kg p.o.

Example 12

Preparation of a Soft Gelatine Capsule

A soft gelatine capsule is prepared comprising the following ingredients:

| Ingredient | Amount per Capsule |
|---|---|
| Carnosol or Rosmanol | 200 mg |
| Lecithin | 50 mg |
| Soy bean oil | 250 mg |

Two capsules per day for 3 months may be administered to a human adult for the treatment of mild chronic dysthymia.

Example 13

Preparation of a Soft Gelatine Capsule

A soft gelatine capsule is prepared comprising the following ingredients:

| Ingredient | Amount per Capsule |
|---|---|
| Carnosol | 100 mg |
| Rosmanol | 100 mg |
| Evening primrose oil | 300 mg |
| Vitamin $B_6$ | 100 mg |

One capsule per day, preferably during the second half of the menstrual cycle, should be taken for 14 days for the treatment of premenstrual syndrome and premenstrual dysphoric disorder.

Example 14

Preparation of a Tablet

A tablet is prepared comprising the following ingredients:

| Ingredient | Amount per tablet |
|---|---|
| Carnosol or Rosmanol | 100 mg |
| Passion flower standardised extract | 150 mg |
| Green Tea Extract, e.g. TEAVIGO ® from DSM Nutritional Products, Kaiseraugst, Switzerland | 150 mg |

For general well-being, energising and stress alleviation, one tablet is taken twice daily for 3 months.

Example 15

Preparation of an Instant Flavoured Soft Drink

| Ingredient | Amount [g] |
|---|---|
| Carnosol or Rosmanol | 0.9 |
| Sucrose, fine powder | 922.7 |
| Ascorbic acid, fine powder | 2.0 |
| Citric acid anhydrous powder | 55.0 |
| Lemon flavour | 8.0 |
| Trisodium citrate anhydrous powder | 6.0 |
| Tricalciumphosphate | 5.0 |
| β-Carotene 1% CWS from DNP AG, Kaiseraugst, Switzerland | 0.4 |
| Total amount | 1000 |

All ingredients are blended and sieved through a 500 µm sieve. The resulting powder is put in an appropriate container and mixed in a tubular blender for at least 20 minutes. For preparing the drink, sufficient water is added to 125 g of the obtained mixed powder, to make up to one litre of beverage.

The ready-to-drink soft drink contains ca. 30 mg carnosol or rosmanol per serving (250 ml). As a strengthener and for general well-being 2 servings per day (240 ml) should be drunk.

Example 16

Preparation of a Fortified Non-Baked Cereal Bar

| Ingredient | Amount [g] |
|---|---|
| Carnosol or Rosmanol | 0.95 |
| Sugar | 114.55 |
| Water | 54.0 |
| Salt | 1.5 |
| Glucose syrup | 130.0 |
| Invert sugar syrup | 95.0 |
| Sorbitol Syrup | 35.0 |
| Palm kernel fat | 60.0 |
| Baking fat | 40.0 |
| Lecithin | 1.5 |
| Hardened palm-oil | 2.5 |
| Dried and cut apple | 63.0 |
| Cornflakes | 100.0 |
| Rice crispies | 120.0 |
| Wheat crispies | 90.0 |
| Roasted hazelnut | 40.0 |
| Skimmed milk powder | 45.0 |
| Apple flavour 74863-33 | 2.0 |
| Citric acid | 5.0 |
| Total amount | 1000 |

Carnosol or rosmanol is premixed with skimmed milk powder and placed in a planetary bowl mixer. Cornflakes and rice crispies are added and the total is mixed gently. Then the dried and cut apples are added. In a first cooking pot sugar, water and salt are mixed in the amounts given above (solution 1). In a second cooking pot glucose, invert- and sorbitol-syrup are mixed in the amounts given above (solution 2). A mixture of baking fat, palm kernel fat, lecithin and emulsifier is the fat phase. Solution 1 is heated to 110° C. Solution 2 is heated to 113° C. and then cooled in a cold water bath. Afterwards solutions 1 and 2 are combined. The fat phase is melted at 75° C. in a water bath. The fat phase is added to the combined mixture of solutions 1 and 2. Apple flavour and citric acid are added to the liquid sugar-fat mix. The liquid mass is added to the dry ingredients and mixed well in the planetary bowl mixer. The mass is put on a marble plate and rolled to the desired thickness. The mass is cooled down to room temperature and cut into pieces. The non-baked cereal bar contains ca. 25 mg carnosol or rosmanol per serving (30 g). For general well-being and energising 1-2 cereal bars should be eaten per day.

What is claimed is:

1. A method for treating an animal, including humans comprising:
   a) administering carnosol and/or rosmanol to a subject experiencing a condition associated with increased neuronal uptake of serotonin, dopamine, or noradrenaline; and
   b) observing a behavioral and/or autonomic effect selected from the group consisting of:
   improved mood/vitality, relief of stress, improved condition, reduced anxiety, reduced obsessive-compulsive behavior, relaxation, improved sleep, alleviated insomnia, enhancer of cognition, maintenance of cognitive wellness and balance, enhanced learning, enhanced language processing, enhanced problem solving, enhanced intellectual functioning, enhanced ability to cope with psychosocial burdens, enhanced attention and concentration, enhanced memory, enhanced mental alertness, enhanced mental vigilance, and stabilized mental status.

2. The method according to claim 1 wherein the carnosol and/or rosmanol is present in a plant extract.

3. The method according to claim 1, wherein the carnosol and/or rosmanol is present in a form selected from the group consisting of: food, feed, dairy products, yoghurts, fortified food, cereal bars, bakery items, cakes, cookies, dietary supplements, tablets, pills, granules, dragées, capsules, effervescent formulations, non-alcoholic drinks, soft drinks, sport drinks, fruit juices, lemonades, near-water drinks, teas, milk-based drinks, liquid foods, soups, and liquid dairy products (muesli drinks).

4. The method according to claim 1 wherein the subject is a human.

5. The method according to claim 1 wherein the subject is selected from the group consisting of pets, companion animals, and farm animals.

* * * * *